(12) United States Patent
Bui et al.

(10) Patent No.: US 10,561,532 B2
(45) Date of Patent: Feb. 18, 2020

(54) METHOD OF RETROFITTING A HEARING PROTECTOR, AND A HEARING PROTECTOR

(71) Applicant: 3M INNOVATIVE PROPERTIES COMPANY, St. Paul, MN (US)

(72) Inventors: Van Cuong Bui, Jököping (SE); Anton J. Hjalmarsson, Bredaryd (SE); Roger Kihlberg, Värnamo (SE); Yossi Sivilia, Ginaton (IL); Sahar Fisch, Arad (IL); Semion Dorfman, Beer Sheva (IL); Guy Shmuel Melamed, Beer Sheva (IL); Beylem Cindoğlu, Ankara (TR); Abir Nagia, Gurgaon (IN); Yuchun He, Hengyang (CN)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/313,495

(22) PCT Filed: Jun. 29, 2017

(86) PCT No.: PCT/IB2017/053937
§ 371 (c)(1),
(2) Date: Dec. 27, 2018

(87) PCT Pub. No.: WO2018/002883
PCT Pub. Date: Jan. 4, 2018

(65) Prior Publication Data
US 2019/0314207 A1 Oct. 17, 2019

(30) Foreign Application Priority Data

Jun. 29, 2016 (EP) ..................................... 16176802
May 16, 2017 (EP) ..................................... 17171288

(51) Int. Cl.
*H04R 1/10* (2006.01)
*A61F 11/14* (2006.01)

(52) U.S. Cl.
CPC ............ *A61F 11/14* (2013.01); *H04R 1/1008* (2013.01); *H04R 1/1041* (2013.01);
(Continued)

(58) Field of Classification Search
CPC ...... H04R 1/10; H04R 1/1008; H04R 1/1041; H04R 1/1075; H04R 1/1083;
(Continued)

(56) References Cited

U.S. PATENT DOCUMENTS 4,572,324 A 2/1986 Fidi
6,829,365 B1 * 12/2004 Kim .................... H04R 1/1058
381/182
(Continued)

FOREIGN PATENT DOCUMENTS

CN 2076834 U 5/1991
CN 201150127 11/2008
(Continued)

OTHER PUBLICATIONS

International Search Report for PCT International Application No. PCT/IB2017/053937, dated Oct. 19, 2017, 4 pages.

*Primary Examiner* — Thang V Tran
(74) *Attorney, Agent, or Firm* — Katherine M. Scholz; Dena M. Ehrich

(57) ABSTRACT

A method of retrofitting a hearing protector with an active communication device. The method has steps of providing a hearing protector, providing the active communication device and retaining the active communication device at the hearing protector. Further, a hearing protector is provided having two generally dome-shaped earmuffs, an active communication device comprising a loudspeaker and electronic
(Continued)

circuitry which comprises a wireless communication interface, and wherein the active communication device has a mounting ring that is retained between an outer shell and a cushioning of the earmuff.

15 Claims, 9 Drawing Sheets

(52) U.S. Cl.
CPC ......... *H04R 1/1075* (2013.01); *H04R 1/1083* (2013.01); *A61F 2011/145* (2013.01); *H04R 2420/07* (2013.01)

(58) Field of Classification Search
CPC ..... H04R 2420/07; H04R 5/033; A61F 11/06; A61F 11/14; A61F 2011/145; A61F 2230/00; A61F 2230/0065
See application file for complete search history.

(56) References Cited

U.S. PATENT DOCUMENTS

| | | | | |
|---|---|---|---|---|
| 7,388,960 | B2* | 6/2008 | Kuo | H04R 1/1041 379/430 |
| 8,209,710 | B2 | 6/2012 | Samson | |
| 8,831,232 | B2 | 9/2014 | Chuang | |
| 2005/0008184 | A1* | 1/2005 | Ito | H04M 1/05 381/370 |
| 2006/0227315 | A1 | 10/2006 | Beller | |
| 2007/0157365 | A1 | 7/2007 | Hansson | |
| 2010/0172519 | A1 | 7/2010 | Kimura | |
| 2013/0025639 | A1 | 1/2013 | Mitchell | |
| 2013/0177165 | A1* | 7/2013 | Oishi | H04R 1/1041 381/74 |
| 2013/0177195 | A1* | 7/2013 | Sze | H04R 1/1033 381/384 |
| 2013/0343565 | A1* | 12/2013 | Ridler | H04R 1/1058 381/74 |
| 2014/0016795 | A1* | 1/2014 | Melamed | H04R 3/00 381/74 |
| 2014/0105414 | A1* | 4/2014 | Rois | H04R 1/1091 381/74 |
| 2014/0153768 | A1 | 6/2014 | Hagen | |
| 2018/0140464 | A1* | 5/2018 | Berto | A61F 11/12 |
| 2019/0110930 | A1* | 4/2019 | Hakansson | A61F 11/14 |

FOREIGN PATENT DOCUMENTS

| | | |
|---|---|---|
| CN | 201967093 | 9/2011 |
| CN | 202859450 | 4/2013 |
| CN | 203138844 | 8/2013 |
| CN | 203632832 | 6/2014 |
| CN | 203915232 | 11/2014 |
| CN | 204050012 | 12/2014 |
| CN | 204291307 | 4/2015 |
| CN | 204350259 | 5/2015 |
| CN | 104735574 | 6/2015 |
| CN | 204394792 | 6/2015 |
| CN | 105472501 | 4/2016 |
| DE | 4329991 | 3/1995 |
| JP | 2016025546 | 2/2016 |
| KR | 2009004749 | 5/2009 |
| KR | 2009004757 | 5/2009 |
| SE | 535706 | 11/2012 |
| TW | 417137 | 12/2011 |
| WO | WO 2005-051255 | 6/2005 |
| WO | WO 2006-058319 | 6/2006 |
| WO | WO 2009-131518 | 10/2009 |
| WO | WO 2014/110873 | 7/2014 |

* cited by examiner

METHOD OF RETROFITTING A HEARING PROTECTOR, AND A HEARING PROTECTOR

CROSS REFERENCE TO RELATED APPLICATIONS

This application is a national stage filing under 35 U.S.C. 371 of PCT/IB2017/053937, filed Jun. 29, 2017, which claims the benefit of European Application Nos. 16176802.3 filed on Jun. 29, 2016, and 171712888.8, filed May 16, 2017, the disclosure of which is incorporated

FIELD OF THE INVENTION

The invention relates to a method of retrofitting a hearing protector with an active communication device and a hearing protector in which an active communication device is mounted.

BACKGROUND ART

Hearing protectors are typically used in noisy environments for protecting a wearer's hearing from noise at potentially harmful noise levels. Typically, hearing protectors have two muffs or caps which cover the ears of the wearer and which are connected to one another by a headband. Each cup further typically is formed by a rigid shell that is furnished with a noise dampening material, for example a foamed material.

There is a general desire to make hearing protectors user-friendly, in particular to encourage persons that are in noisy environments for longer times to actually wear the protectors. While noise dampening is the essential purpose of a hearing protector, there is often a need for the wearer to hear certain sounds from the environment, like acoustic signals, instructions, or conversations. Further, there is often a desire for the wearer to use the hearing protector as headset for radio or telephone applications.

There are active hearing protectors on the market which have passive noise dampening properties and additionally are configured to transmit sounds from the environment into the ear cup via active electronics connected to a microphone outside the ear cup and a loud speaker inside the ear cup. Such hearing protectors are typically set up so that the active sound transmission is restricted to a pre-determined level with respect to the human hearing. Sound levels from the environment that exceed that pre-determined level are dampened due to the passive dampening properties of the hearing protector.

WO 2006/058319 for example discloses a hearing protector device including a sound attenuating body and an electronic unit having a microphone, an amplifier, and a loudspeaker, where the electronic unit is selectively activated and, when activated, receives sound from an ambient environment, amplifies a frequency range of the received sound corresponding to a frequency range of human speech, and varies said amplification such that a total level of sound passing through the body and through the electronic unit does not exceed a maximum predetermined sound level.

Although existing active hearing protectors have a variety of advantages there is still a need for a hearing protector which is of preferably high quality and durable but relatively inexpensive. Further, such a hearing protector desirably can be serviced relatively conveniently.

SUMMARY OF THE INVENTION

The Invention relates to a method of retrofitting a hearing protector with an active communication device. The method comprises the steps of:
providing a hearing protector that has two generally dome-shaped earmuffs, each earmuff forming toward an ear facing side of the earmuff a space for a wearer's ear, at least one of the earmuffs comprises an outer shell and a cushioning arranged adjacent the ear facing side;
providing the active communication device, the active communication device comprising a loudspeaker and electronic circuitry which comprises a wireless communication interface, the electronic circuitry being configured to drive the loudspeaker based on information received via the wireless communication interface, wherein the active communication device comprises a mounting ring;
mounting the mounting ring between the outer shell and the cushioning; and
retaining the active communication device at the hearing protector so that the loudspeaker is arranged within the space formed the earmuff.

The invention is advantageous in that it allows retrofitting of particularly passive hearing protectors by an active communication device generally independent from the type, brand or configuration of the passive hearing protectors. Further, the invention allows for reversibly retrofitting of passive or active hearing protectors by an active communication device. Accordingly in a work environment in which mainly passive hearing protection is used, a few of the hearing protectors used therein may be retrofitted selectively as needed. Further, the invention allows for easily replacing any active communication device by another active communication device, for example for recharging, for repair or maintenance. Thus, the invention helps to minimize costs in the use of hearing protectors while taking advantage from active communication technology in combination with hearing protection.

In a preferred embodiment the hearing protector is a passive hearing protector. A passive hearing protector typically in particular does not comprise a loudspeaker. Further, a passive hearing protector typically does not comprise electronics for driving the loudspeaker. It is noted that although the invention preferably relates to retrofitting a passive hearing protector, the retrofitting of an active hearing protector is covered. For example, an active hearing protector being configured with a so-called noise cancellation function may be retrofitted with an active communication device. The noise cancellation function is typically provided by electronic components comprising a microphone for picking up sound from the exterior of the earmuff and a loudspeaker for emitting sounds toward the wearer ear within the earmuff and components for converting the sound picked up by the microphone into the sound emitted by the loudspeaker. Typically the conversion includes a phase shift between the sound picked up and the sound emitted so that the acoustic waves emitted by the loudspeaker compensate with any sound penetrating into the earmuff toward a sound amplitude that is lower than the penetrating sound amplitude. The noise cancellation function may further include active sound transmission at lower noise levels and sound squelching above a predetermined noise level. Such sound transmission provides for picking up sounds by the microphone and emitting of the sound via the loudspeaker at a predetermined maximum noise level. Accordingly, noise peaks and higher sound levels are automatically cut off or emitted at a reduced noise amplitude.

Preferably the active communication device is provided as a structurally separate component from the hearing protector. This does not exclude that the active communication device may be provided in one package with the hearing protector. However, initially (before retrofitting) the active communication device and the hearing protector are preferably not directly structurally mounted to each other and the hearing protector can be used without the active communication device.

Typically each of the two earmuffs comprise an outer shell and a cushioning arranged adjacent the ear facing side. Each outer shell is preferably inwardly provided with a noise dampening material. Such a dampening material may for example be made of a foamed plastic material. The cushioning serves for sealing the space formed by the respective earmuff at a wearer's head when the hearing protector is worn by the wearer. Preferably the cushioning is shaped to extend around a wearer's ear. So configured earmuffs are also referred to as "over ear" ear muffs in the field of hearing protectors and headphones. The cushioning is preferably generally oval-shaped.

The ring-shape of the mounting ring preferably generally corresponds to the ring-shape of the cushioning. Further, by the step of mounting the mounting ring between the outer shell and the cushioning the active communication device is preferably retained at the hearing protector so that the loudspeaker is arranged within the space formed the earmuff. Accordingly, the active communication device comprises the mounting ring that is retained between the outer shell and the cushioning in such a way that the loudspeaker is arranged within the space formed by the earmuff.

In a further embodiment the earmuff comprises a spacer ring arranged between the cushioning and the outer shell. In this embodiment the method may further comprise the step of replacing the spacer ring by the mounting ring. Preferably the mounting ring is configured to be mounted with the cushioning. For example the cushioning and the mounting ring may be configured to in combination form a snap connection with each other. Alternatively or additionally the mounting ring and the cushioning may be mounted with each other by adhesive bond. Preferably the mounting ring is further configured to be mounted with the outer shell. For example the outer shell and the mounting ring may be configured to in combination form a snap connection with each other. Alternatively or additionally the mounting ring and the outer shell may be mounted with each other by adhesive bond. Other connections, like for example press fittings, interlocks, hook and loop fasteners etc. are possible as appropriate.

In one embodiment the active communication device further has a microphone. The microphone and the electronic circuitry are preferably connected or connectable such that the electronic circuitry can receive information from the microphone and transmit the information via the wireless communication interface. The active communication device may further have two (or more) microphones for maximizing the sound quality of the sound picked up.

In a further embodiment the active communication device comprises a first part and a second part. The first part may comprise the loudspeaker and the second part may comprise the microphone. The first part is preferably arranged within the space formed by the earmuff. The second part is preferably arranged outside the space formed by the respective earmuff. Accordingly, a wearer of the hearing protector is enabled to hear sounds emitted by the loudspeaker while wearing the hearing protector. Further, the wearer of the hearing protector is enabled to communicate via the microphone and the loudspeaker via the wireless communication device. In addition a wearer of the hearing protector may be enabled to clearly hear sounds from outside the earmuff picked up by the microphone while wearing the hearing protector. Therefore the electronic circuitry may be configured to limit the sound level emitted via the loudspeaker to a pre-determined maximum sound level. Thus, any sound levels that are potentially harmful for the wearer's ear can be cut off to an acceptable level.

In one embodiment the first and second part form parts of one common structural entity. For example the active communication device may comprise the mounting ring with the first part attached to or formed with the mounting ring. The second part may also be attached to or formed with the mounting ring, optionally via shaft which extends between the mounting ring and the second part or between the first part and the second part.

In one embodiment the first and second part are structurally separated and configured for a wireless communication with each other. For example the first part may have the wireless communication device and that wireless communication device may be used for communication with an external device (like a mobile phone or radio unit) as well as for communication with the first part. The wireless communication device may be based on Bluetooth™. The second part may have a further communication device for communication with the first part. The further communication device of the second part may optionally additionally be used for communication with an external device (like a mobile phone or radio unit).

In one embodiment the electronic circuitry is arranged inside boundaries of the mounting ring. Further, at least a part of the electronic circuitry may be arranged between the outer shell and the cushioning. The mounting ring may have a cavity within which the electronic circuitry or at least part of the electronic circuitry is arranged. A first printed circuit board may be provided in the cavity which comprises the electronic circuitry (or part of it). The cavity may be covered or sealed by a cover. Hence, the electronic circuitry (or part of it) may be encapsulated within the sealing ring.

In a further embodiment the active communication device has a battery, for example a rechargeable battery. The battery is preferably arranged piggyback behind the loudspeaker. Further a second printed circuit board carrying part of the electronic circuitry may be arranged between the battery and the loudspeaker. The first and second printed circuit board are preferably electrically connected via two or more wires, or a flexible printed circuit board.

In a further embodiment the first and second printed circuit board comprise a plurality of electronic components. The electronic components are preferably positioned relative to the first and/or second printed circuit board based on the available space within the earmuff. Accordingly the positioning of the electronic components may not be optimized only for compactness, but in addition for using available space and avoiding restricted space. This is in contrast to prior art electronic circuit boards which are typically optimized only for compactness of the overall printed circuit board.

In a further aspect the invention relates to a hearing protector that comprises:
two generally dome-shaped earmuffs forming toward an ear facing side a space for a wearer's ear, wherein at least one of the earmuffs further comprises an outer shell and a cushioning arranged adjacent the ear facing side; and an active communication device comprising a loudspeaker and electronic circuitry which comprises a wireless communication interface, the electronic circuitry being configured to drive the loudspeaker based on information received via the wireless communication interface, and wherein the active communication device comprises a mounting ring that is retained between the outer shell and the cushioning, and wherein the loudspeaker is arranged within the space formed by one of the earmuffs.

The hearing protector can preferably be obtained by the method of the invention.

In one embodiment the mounting ring has a first retention structure being retained with a corresponding retention structure at the outer shell. Further, the mounting ring and the cushioning are preferably retained with each other.

In a further embodiment the active communication device comprises one, two or more microphones. The microphone and the electronic circuitry are preferably connected or connectable such that the electronic circuitry can receive information from the microphone and transmit the information via the wireless communication interface. The microphone is preferably arranged on an outer peripheral side of the mounting ring. The microphone may be arranged within a plastically bendable microphone holder. The microphone holder is preferably elongated for positioning the microphone in the vicinity of a wearer's mouth. Further, the microphone holder is preferably plastically bendable.

In an embodiment the hearing protector comprises two microphones arranged adjacent each other. The hearing protector may further comprise a control button which is connected or connectable to the electronic circuitry for switching the microphone(s) on or off. The electronic circuitry may be configured to interpret different operations on the control button to activate corresponding different functions. Accordingly, the control button may be further used to initiate pairing of the wireless communication device with an external device or for muting or unmuting the active communication device. The active communication device preferably has a battery for powering the electronic circuitry. Such battery is preferably rechargeable, but may also be replaceable.

In a further embodiment the active communication device has a control light or for indicating a status of the active communication device. For example the control light may be used to indicate a stand-by mode in which the active communication device is switched off, an active mode in which the active communication device is switched on, a disconnected mode in which the active communication device is ready for pairing, a connected mode in which the active communication device is paired and a low battery mode in which the active communication device signals low power of the battery.

In a further embodiment the electronic circuitry is arranged inside boundaries of the mounting ring. In particular at least a part of the electronic circuitry is arranged between the outer shell and the cushioning. Accordingly, the electronic circuitry is accommodated within boundaries of the earmuff Therefore a relative compact design is achieved. Further, the electronic circuitry is protected within the earmuff. The arrangement between the cushioning and the outer shell is particularly advantageous in that the acoustic properties of the earmuff are not or not substantially affected. For example, it is not necessary to create additional space for the electronic circuitry within the earmuff, nor is there a need to locate part of the electronic circuitry outside the earmuff.

The mounting ring may have a cavity within which the electronic circuitry or at least part of the electronic circuitry is arranged. A first printed circuit board may be provided in the cavity which comprises the electronic circuitry (or part of it). The cavity may be covered or sealed by a cover. Hence, the electronic circuitry (or part of it) may be encapsulated within the sealing ring.

In a further embodiment the battery is arranged piggyback behind the loudspeaker. Further a second printed circuit board carrying part of the electronic circuitry may be arranged between the battery and the loudspeaker. The first and second printed circuit board are preferably electrically connected via two or more wires, or a flexible printed circuit board.

DETAILED DESCRIPTION OF THE INVENTION

Figure 1:
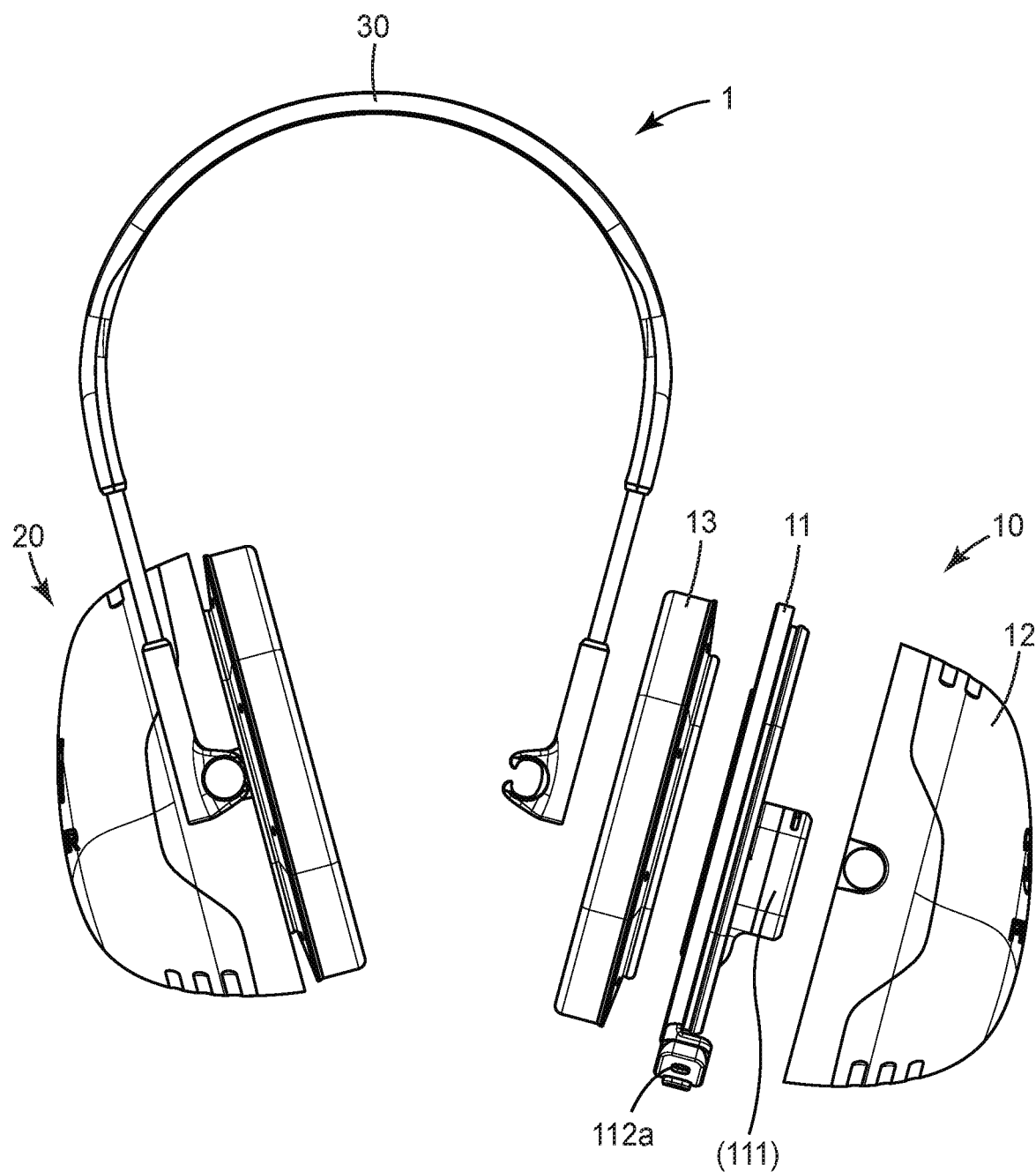
FIG. 1 is a partial exploded view of a hearing protector according to an embodiment of the invention.

FIG. 1 shows a hearing protector 1 according to the invention. The hearing protector 1 comprises a first earmuff 10 and a second earmuff 20. The first earmuff 10 has is illustrated as exploded view for the sake explanation only, although it is typically assembled. The first earmuff 10 is an active earmuff, whereas the second earmuff 20 is a passive earmuff. This means that the first earmuff 10 has an active communication device 11 that has electronic circuitry, a loudspeaker 111 (not visible in this view) and a microphone 112a as explained in further detail below. In the example the second earmuff 20 has no active communication device, although in another example both earmuffs may have an active communication device.

The first earmuff 10 has an outer shell 12 and a cushioning 13. The outer shell 12 is provided with noise dampening properties. For example, the outer shell 12 may be formed of a rigid material and may be provided with a noise dampening material (not illustrated) inwardly. Such rigid material may be a plastic material, for example acrylonitrile butadiene styrene (ABS). The noise dampening material may comprise a foamed plastic material, for example Polyethylene (PE). The cushioning 13 may comprise a soft material that enables the cushioning 13 to adapt to a wearer's head around the wearer's ear. Thus, the cushioning 13 can seal at the wearer's head. The soft material of the cushioning 13 may comprise a foamed plastic material, for example Polyethylene (PE). Further, the cushioning 13 comprises a sheath that encloses the soft material. The sheath may be a plastic material selected from among polyvinylchloride (PVC) and thermoplastic polyurethane (TPU). The skilled person will recognize other configurations for providing an outer shell having noise dampening properties or a cushioning that can adapt and seal to a wearer's head. Accordingly the earmuff 10 forms a noise dampened space for receiving a wearer's ear.

The hearing protector 1 further has a headband 30 to which the first and second earmuffs 10, 20 are attached. The first and second earmuffs 10, 20 in the example are hingedly attached at opposite side s of the headband 30. Thus, the earmuffs can automatically freely orient relative to the wearer's head when the hearing protector 1 is worn by a wearer. Such free orientation provides for the cushioning 13 to uniformly seal with the wearer's head along a circumference of the cushioning 13.

In the example, the hearing protector 1 is obtained from a purely passive hearing protector by retrofitting the hearing protector with the active communication device 11. The method of retrofitting comprises the step of mounting the active communication device 11 between the outer shell 12 and the cushioning 13. Further, the method comprises the step of separating the cushioning 13 from the outer shell 12 and assembly the active communication device 11 between the outer shell 12 and the cushioning 13. It is noted that in another example the hearing protector may also be provided in the configuration as shown by a manufacturer of the hearing protector 1.

Figure 2:
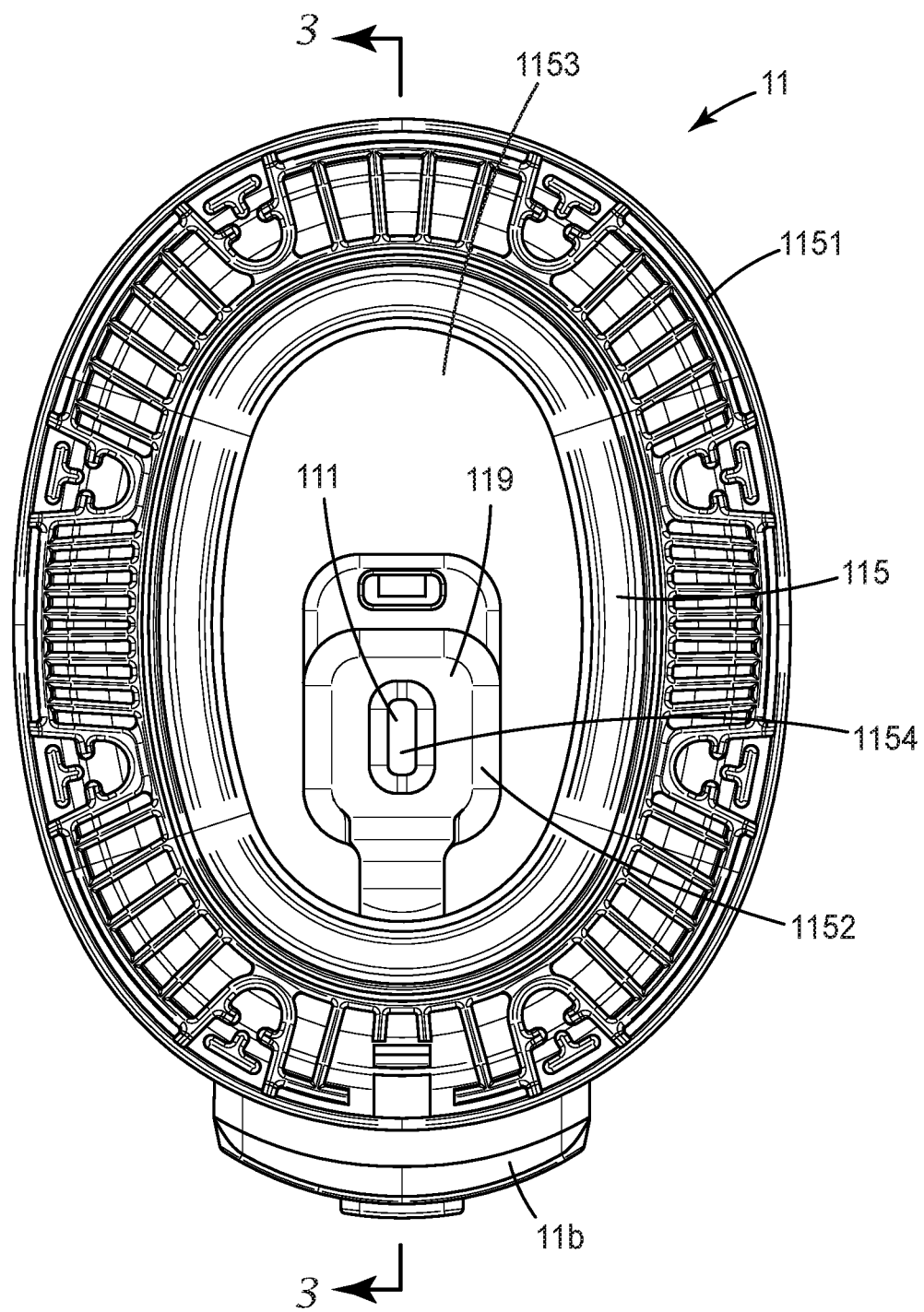
FIG. 2 is a front view of an active communication device according to an embodiment of the invention.

FIG. 2 shows a front view of the active communication device 11 in a preferred embodiment of the invention. The active communication device 11 has a support structure 115 which forms a mounting ring 1151. The mounting ring 1151 is shaped and sized essentially in accordance to the shape and size of the cushioning (not illustrated in this view). Therefore the mounting ring 1151 is adapted for carrying the cushioning. The mounting ring 1151 in the example further forms a major through-hole 1153. The skilled person will however recognize that the through-hole is optional provided that a wearer's ear can be received within the earmuff, for example within a through-hole of the cushioning. The support structure 115 further forms a loudspeaker holder 1152 that houses the loudspeaker 111 (visible in FIG. 3). The loudspeaker holder 1152 protrudes from the mounting ring 1151 and overhangs the major through-hole 1153. The loudspeaker holder 1152 thus overlaps the major through-hole 1153 and forms a sound opening 1154 within the area of the through-hole 1153. The active communication device 11 is configured for assembly in the earmuff such that the sound opening 1154 faces toward an ear facing side of the earmuff. Accordingly, when the earmuff is placed over a wearer's ear the sound opening essentially faces the wearer's ear canal. The loudspeaker holder 1152 in this example further forms a first part 11a of the active communication device 11, which is arranged within the earmuff 10 when assembled. The mounting ring 1151 in the example is based on a frame construction forming a number of ear facing recesses within the mounting ring. Thus, the mounting ring forms an air permeable interface toward the side at which the cushioning is received on the mounting ring 1151. This prevents the mounting ring from sealing the venting openings and enables air to flow through via recesses toward or from the air cushioning. Typically, an air cushioning comprises a sheath that encloses a resilient foamed material. That sheath typically has venting openings that allow for air communication through the sheath as the foamed material is compressed or released. These venting openings are typically oriented toward an inside of the outer shell of the earmuff. In the example, the cushioning is arranged with the venting openings facing the mounting ring 1151 so that the venting openings are in air communication with the recesses of the mounting ring 1151. Therefore, the air communication provided by any venting openings in the cushioning is maintained by the mounting ring 1151. On the other hand any undesired substances like dust, dirt or liquids are hindered in directly penetrating in to the cushioning from the outside of the earmuff, particularly if the earmuff is worn by a wearer.

The support structure 115 is preferably made of a plastic material, for example acrylonitrile butadiene styrene (ABS). In the example the support structure comprises a first element 115a (see FIG. 3) that is monolithically formed (preferably injection molded) in one piece and a second element 115b (see FIG. 3) that is also monolithically formed (preferably injection molded) in one piece. The first and second elements 115a, 115b can be assembled with each other so as to form in combination a housing for the loudspeaker 111. The first element 115a and a third element 115c can be assembled with each other to form in combination a housing for, inter alia, microphones (112a, 112b in FIG. 4). The skilled person will recognize different configurations for the support structure. Generally, the support structure is preferably configured for forming assembly interfaces to the outer shell and the cushioning, respectively. Further, the support structure is preferably configured to carry and/or to house any electronic circuitry, one or more loudspeakers, one or more microphones and one or more control buttons.

Figure 3:
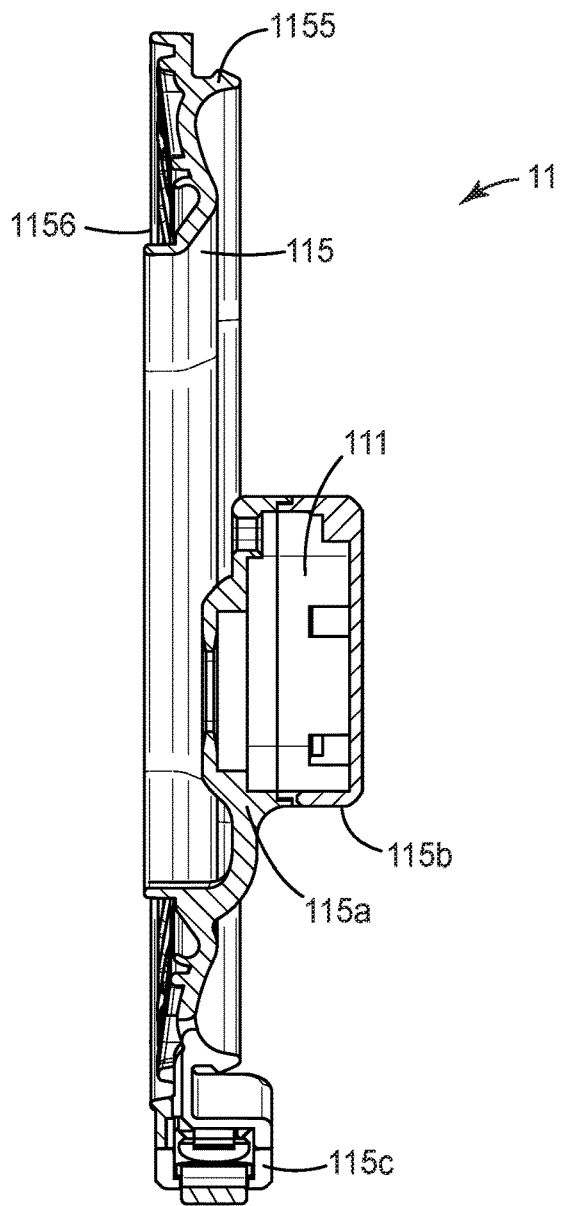
FIG. 3 is a side view of an active communication device according to an embodiment of the invention.

FIG. 3 shows a cross-sectional side view of the active communication device 11. In particular, the support structure 115 of the active communication device 11 comprises a first retention structure 1155. The first retention structure 1155 in the example is formed by a circumferential flange. The outer shell of the hearing protector preferably has a corresponding first counter-structure (not illustrated). The first retention structure and the first counter-structure are preferably configured to form a releasable snap connection with each other. In particular, the outer shell of the hearing protector in the example has receptacle for receiving the flange. Thereby the flange and the receptacle are shaped and sized so that the flange can be snapped into the receptacle. The skilled person will be aware of several configurations for providing a snap connection for example one or more mushroom-shaped pins in combination with corresponding holes, or one or more hooks in combination with corresponding recesses. The male and female structures may be either on the outer shell or the support structure 115 or a combination thereof.

The support structure 115 further has a second retention structure 1156 for retaining the cushioning. Alternatively or additionally the cushioning may be bonded to the support structure 115 by an adhesive.

Figure 4:
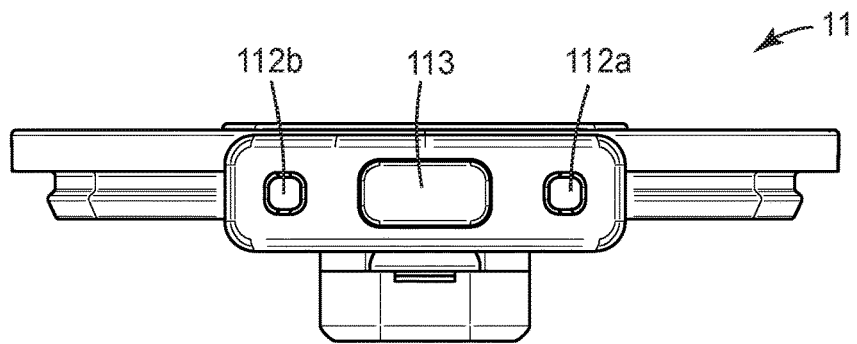
FIG. 4 is a bottom view of an active communication device according to an embodiment of the invention.

FIG. 4 shows the active communication device 11 in a bottom view. The active communication device 11 comprises two microphones 112a, 112b and a control button 113. The microphones 112a, 112b and the control button are arranged in a second part 11b of the active communication device 11 and are arranged outside the space formed by the earmuff 10. Thus, the microphones 112a, 112b can pick up sounds from outside that space, in particular from the environment of the hearing protector.

The function of the active communication device 11 of the example is as follows:

The active communication device 11 has electronic circuitry which is configured to control the loudspeaker (111 in FIG. 3) and the microphones 112a, 112b. The electronic circuitry is also configured to receive input signals from the control button 113. Further, the electronic circuitry implements a wireless communication interface, in the example a Bluetooth™ interface. The electronic circuitry is configured to control the loudspeaker based on information received via the wireless communication interface. In particular the electronic circuitry is configured to convert any information which encode a sound and received via the wireless communication interface into electric signals for causing the loudspeaker to generate the respective sounds. Further, the electronic circuitry is configured to receive signals from the microphone and to convert these signals into sound information that is transmittable or transmitted via the wireless communication interface. The active communication device 11 can for example be coupled via the wireless communication interface to an external device, for example a mobile phone or a radio unit for communication. Therefore, the active communication device 11 enables a wearer of the hearing protector to communicate while wearing the hearing protector. In the example the control button 113 can be operated to trigger multiple functions. Firstly, the control button 113 may be operated for switching the active communication device on or off. For switching the device on or off the control button 113 may be pressed for predetermined duration, for example several seconds. The active communication device 11 comprises a control light and the control light indicates whether the device is switched on or off. In the example the control light is integrated in the control button. In particular, the control button is illuminateable, preferably by an LED or other low energy consuming lighting. For example, the control light may be lighting continuously during the active communication device is switched on and active for speaking and listening. A short push on the control button may switch the active communication device 11 on mute so that sound picked up by the microphone is not transmitted via the wireless active communication device. The mute mode may be indicated by the control light by a low frequency flashing, for example. Further, the electronic circuitry may indicate the switching into mute acoustically via the loudspeaker, for example by an electronic announcement or a particular sound. The mute mode may be ended by another short push on the control button 113. Other functions may be implemented in a similar fashion. For example, the control button 113 may be operated to initiate pairing of the wireless communication interface with an external device. The control light may further be used to indicate different operation modes or error states. For example, the active communication device 11 has a battery, preferably a rechargeable battery. The control light may be used to indicate a low battery state of that battery, for example by high frequency flashing. The skilled person will recognize other functions that may be triggered by the control button and corresponding indications via the control lighting. Further, instead of a single control button and a single control light multiple buttons, switches and lights may be used with the present invention.

The electronic circuitry may be configured to output sound received via the microphone directly on the loudspeaker so that the wearer of the hearing protector can hear surrounding sounds. The electronic circuitry is however configured to limit the output sound to an acceptable level for the wearer. This means that the electronic circuitry is configured such that it does not output any sound above a certain pre-determined sound level. Thus, the hearing protection provided by the hearing protector can be maintained although the active communication device is used. Further, the electronic circuitry may have a noise cancellation function as described above.

The active communication device 11 may be provided in different structural embodiments but with the same electronic functionality as further described in the following.

Figure 5:
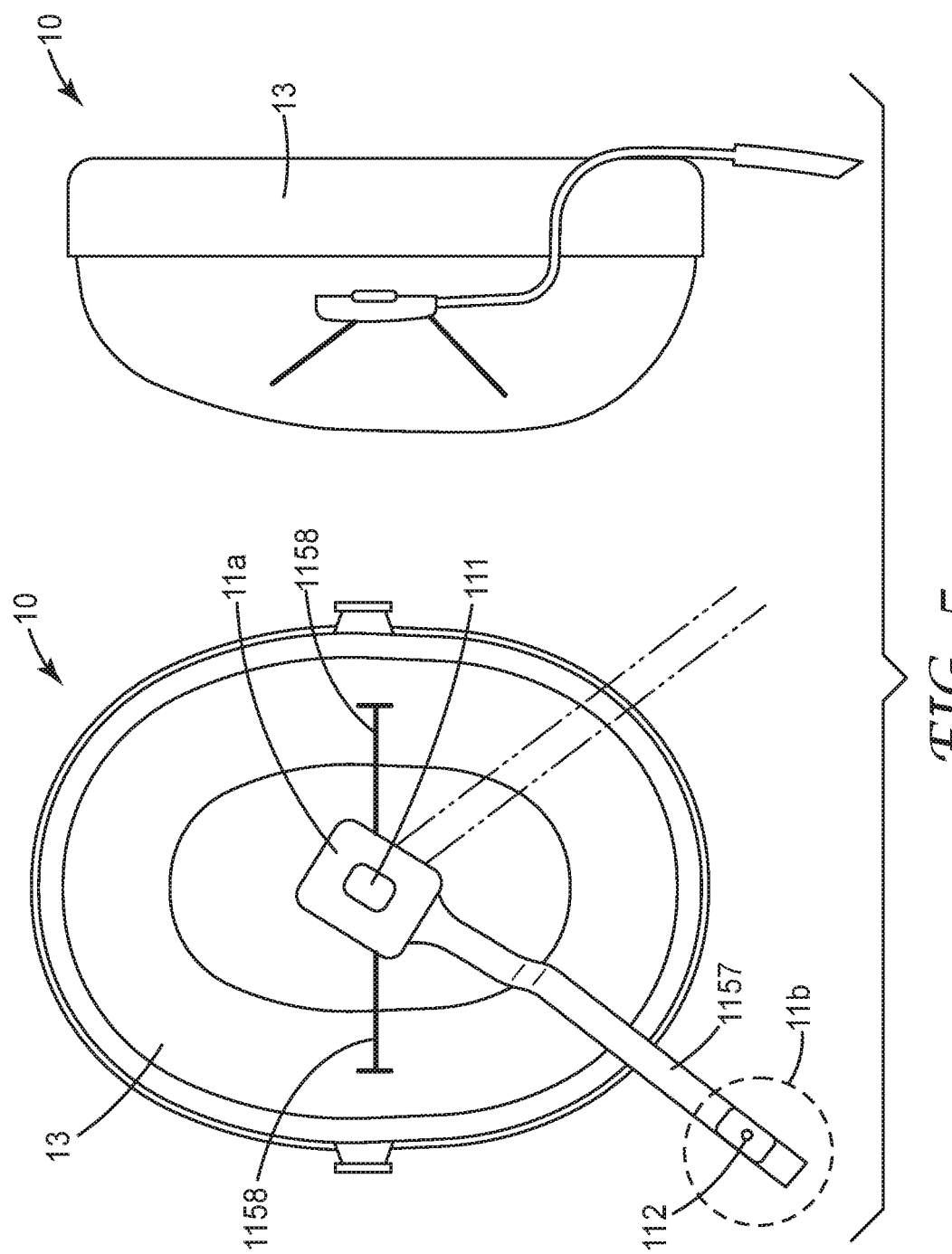
FIG. 5 is a front and side view of an earmuff including an active communication device according to an embodiment of the invention.

FIG. 5 shows an example of an earmuff 10 for a hearing protector in a front and a side view. An active communication device 11 is attached at the earmuff 10. In this example the active communication device 11 has a first part 11a which comprises a loudspeaker 111 and a second part 11b which comprises a microphone 112. The first part 11a is arranged within the earmuff 10 and the second part 11b is arranged outside the earmuff 10. The active communication device 11 further has electronic circuitry having a functionality as described in the example shown in FIGS. 1 to 4. In the example the first and second part 11a, 11b are structurally connected by a shaft 1157 which extends between the first and second part 11a, 11b. The active communication device 11 of this embodiment can be assembled to the earmuff 10 without disassembling the earmuff 10. In particular, the first part 11a of the active communication device 11 is arranged within the space for the wearer's ear formed by the earmuff 10, and the shaft 1157 extends from the space via the outer side of the cushioning 13 toward the second part 11b. Accordingly, the shaft 1157 is directly arranged between the wearer's head and the cushioning when the hearing protector is worn by the wearer. The shaft 1157 extends at a generally flat cross-section, in particular a lenticular cross-section. The active communication device 11 is arranged at the earmuff 10 such that the shaft 1157 lies flat on the cushioning 13. Therefore the cushioning 13 can conform to and seal with the wearer's head although the shaft 1157 is arranged between. For mounting the active communication device 11 to the earmuff 10 the active communication device 11 may be provided with one or more retainers 1158 which can be clamped behind the cushioning or which retain at the dampening material within the earmuff. However in one embodiment the active communication device 11 may be held in place only by a compression force on the shaft 1157 between the cushioning 13 and the wearer's head when the hearing protector is worn by the wearer.

Figure 6:
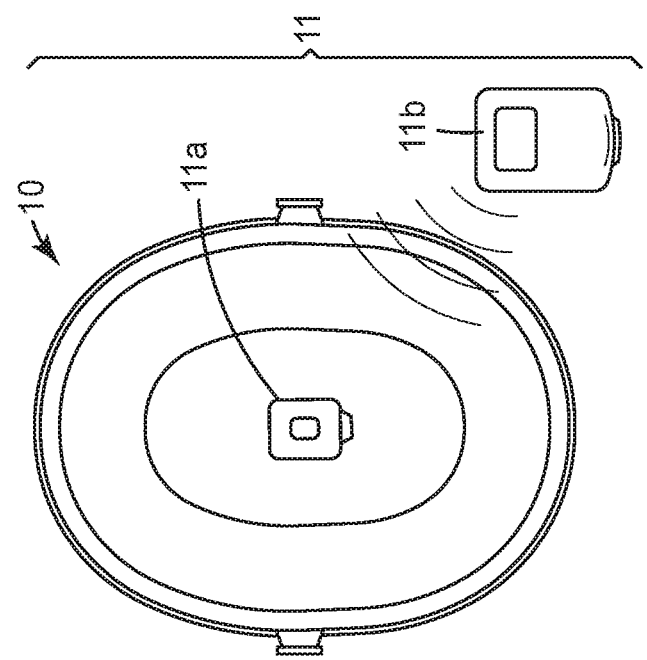
FIG. 6 is a front and side view of an earmuff including an alternative active communication device according to an embodiment of the invention.

FIG. 6 shows a further example of an earmuff 10 for a hearing protector in a front and a side view. The earmuff 10 is provided with an active communication device 11 having a first part 11a which comprises a loudspeaker 111 and a second part 11b which comprises a microphone 112. The active communication device 11 further has electronic circuitry (not illustrated in detail) having a functionality as described in the example shown in FIGS. 1 to 4. The first part 11a is arranged within the earmuff 10 and the second part 11b is arranged outside the earmuff 10. In the example the first and second part 11a, 11b are structurally separate. This means that the first and second part 11a, 11b are not structurally connected. In this embodiment the first part 11*a* of the active communication device 11 can be assembled to the earmuff 10 without disassembling the earmuff 10. The first part 11*a* is arranged within the space for the wearer's ear formed by the earmuff 10. The second part 11*b* is freely movable outside the earmuff 10. The first and the second part 11*a*, 11*b* are connected via a wireless connection. In this embodiment each of the first and the second part 11*a*, 11*b* have a battery and electronic circuitry for enabling and controlling a communication between the first and second part 11*a*, 11*b*. The electronic circuitry of at least one of the first and second part 11*a*, 11*b* further implements the wireless communication interface for connecting with an external device, as described above.

For mounting the first part 11*a* to the earmuff 10 the first part 11*a* may be provided with one or more retainers which can be clamped behind the cushioning or which retain at the dampening material within the earmuff 10.

Figure 7:
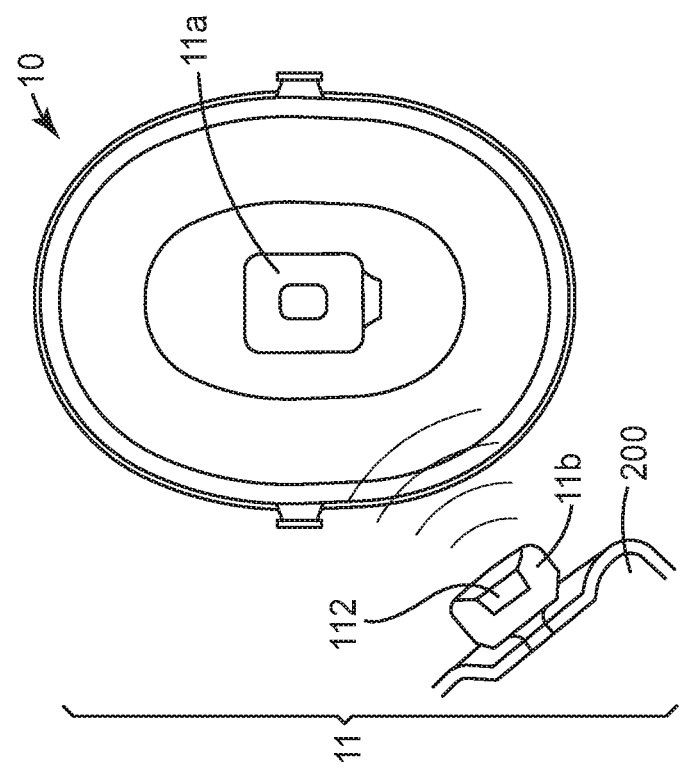
FIG. 7 is a front and side view of an earmuff including another alternative active communication device according to an embodiment of the invention.

FIG. 7 shows an embodiment in which a first part 11*a* is similar or identical with the corresponding first part of the example in FIG. 6, but in which a second part 11*b* is provided by an external device 200 like a mobile phone or a radio unit. In this example, a microphone 112 which is part of the external device 200 is used for transmitting sound information toward the first part 11. In this example the active communication device 10 is formed by the external device 200 (also forming the second part 11*b*) and the first part 11*a*. The Wireless Communication Interface is Provided in the external device 200 which typically is equipped with such an interface (for example a Bluetooth™ interface) per default, and further in the first part 11*a*. Therefore the external device and the first part 11*a* are enabled for communication with one another via the wireless communication interfaces.

Figure 8:
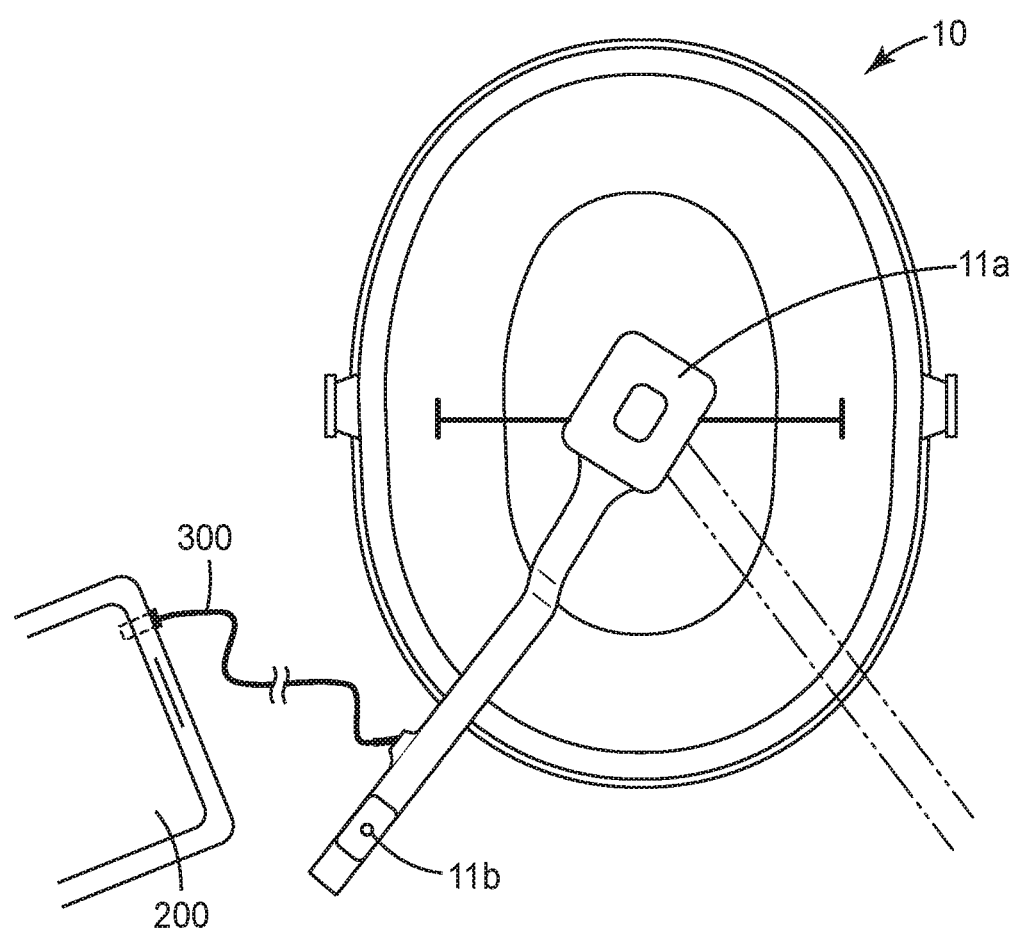
FIG. 8 is a front and side view of an earmuff including still another alternative active communication device according to an embodiment of the invention

FIG. 8 shows an embodiment in which an active communication device 11 is structurally identical with the device of the example shown in FIG. 5 except for a wired communication interface being provided therein. The wired communication interface is provided by a cable connection 300 for connecting the active communication device 11 to an external device 200. The functionality of the active communication device 11 is identical to the functionality of the active communication device described in FIG. 5 except for the wired communication interface that may be provided in addition or instead of a wireless active communication device. In one example the active communication device 11 is only powered by the external device 200, whereas in another example the active communication device 11 may be powered by an internal battery as described.

Figure 9:
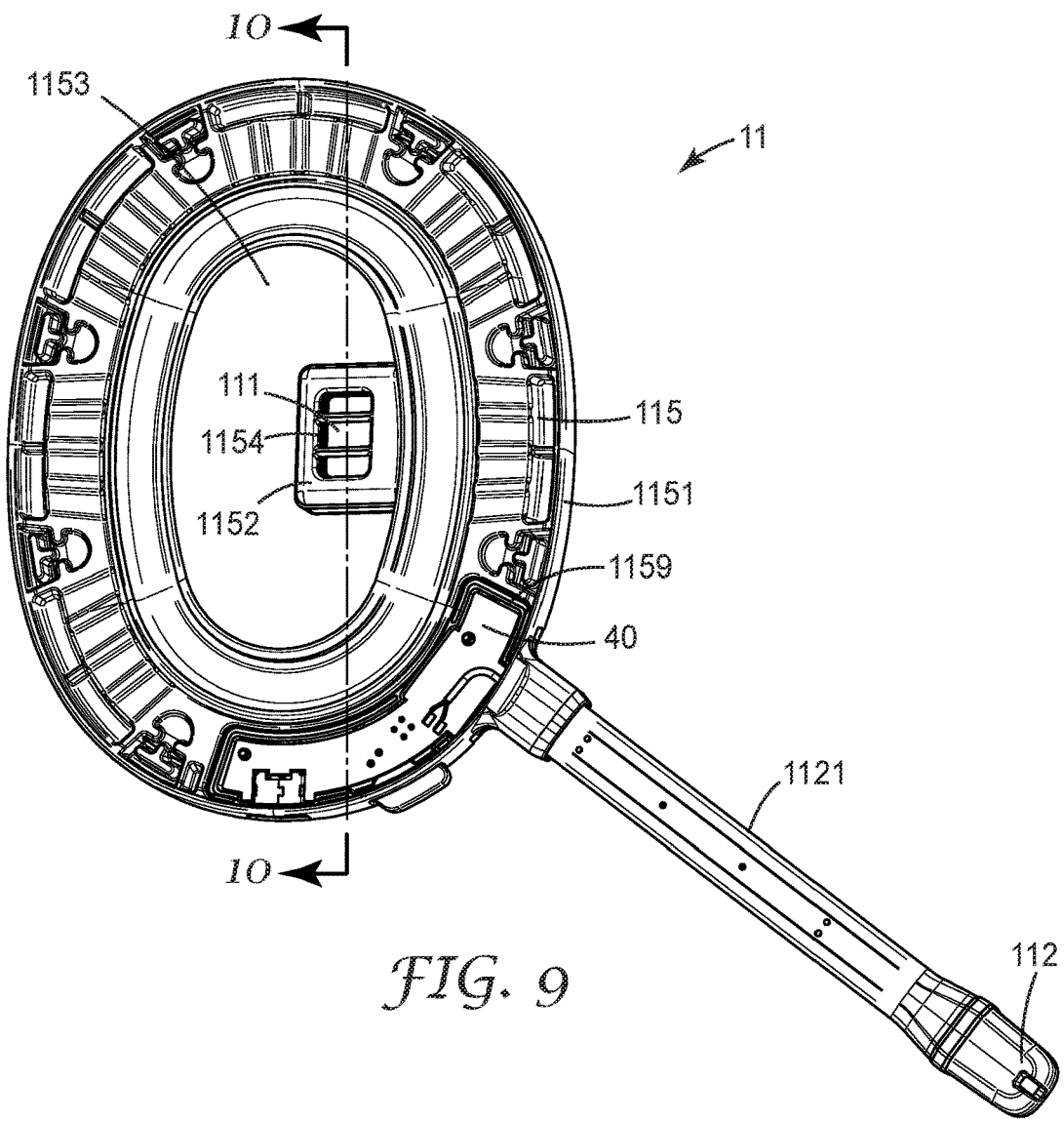
FIG. 9 is a front view of an active communication device according to an embodiment of the invention

FIG. 9 shows a front view of an alternative active communication device 11. The active communication device 11 has a support structure 115 which forms a mounting ring 1151. The mounting ring 1151 is shaped and sized essentially in accordance to the shape and size of the cushioning (not illustrated in this view) of the hearing protector 1. In particular the mounting ring 1151 is configured for carrying the cushioning. The mounting ring 1151 in the example further forms a major through-hole 1153. The support structure 115 further forms a loudspeaker holder 1152 that houses the loudspeaker 111. The loudspeaker holder 1152 protrudes from the mounting ring 1151 and overhangs the major through-hole 1153. The loudspeaker holder 1152 thus overlaps the major through-hole 1153. Further, the loudspeaker holder 1152 forms a sound opening 1154 within the area of the through-hole 1153. In the example the sound opening 1154 comprises three individual openings. However, more or less openings may be provided as appropriate. The active communication device 11 is configured for assembly in the earmuff such that the sound opening 1154 faces toward an ear facing side of the earmuff. Accordingly, when the earmuff is placed over a wearer's ear the sound opening essentially faces the wearer's ear canal.

As described above in FIG. 2 the mounting ring 1151 in this example is also based on a frame construction forming a number of ear facing recesses within the mounting ring, to prevent the mounting ring from sealing venting openings in the cushioning.

The support structure 115 is preferably made of a plastic material, for example acrylonitrile butadiene styrene (ABS). In the example the support structure comprises a first element 115*a* (see FIG. 10) that is monolithically formed (preferably injection molded) in one piece and a second element 115*b* (see FIG. 10) that is also monolithically formed (preferably injection molded) in one piece. The first and second elements 115*a*, 115*b* can be assembled with each other so as to form in combination a housing for the loudspeaker 111.

In the example the support structure 115 further forms a cavity 1159 in which a first printed circuit board 40 is accommodated. The first printed circuit board 40 comprises electronic circuitry for controlling the active communication device 11. The support structure 115 has a cover 115*d* (not present in FIG. 9 but shown in FIG. 10) which closes the cavity 1159 and preferably seals the cavity 1159. Thus, the electronic circuitry is encapsulated, preferably hermetically encapsulated within the support structure 115.

Further, the active communication device 11 has a battery 41 (which is preferably a rechargeable battery) for powering the active communication device 11. In the example the battery 41 is arranged behind the loudspeaker 111 within the loudspeaker holder 1152. This means that the loudspeaker 111 is arranged toward the ear facing side and the battery is arranged toward the opposite side. A second printed circuit board 42 is arranged in the loudspeaker holder 1152. In particular the second printed circuit board 42 is arranged between the battery 41 and the loudspeaker 111. The second printed circuit board 42 comprises electronic circuitry, for example for controlling the battery 41 (for example during charging or during use of the active communication device 11) and or for controlling the loudspeaker 111. The first and second printed circuit board are electrically cooperating. In particular, the first and second printed circuit board are interconnected by two or more wires.

The active communication device further comprises a microphone 112, which in the example is arranged in a free end portion of a microphone holder 1121. The microphone holder is elongated for positioning the microphone 112 in the vicinity of a wearer's mouth. Further, the microphone holder 1121 is preferably plastically bendable. Thus, the microphone holder is user-adjustable in its position. As described above instead of one microphone two (or more) microphones may be accommodated in the free end portion of the microphone holder 1121.

Figure 10:
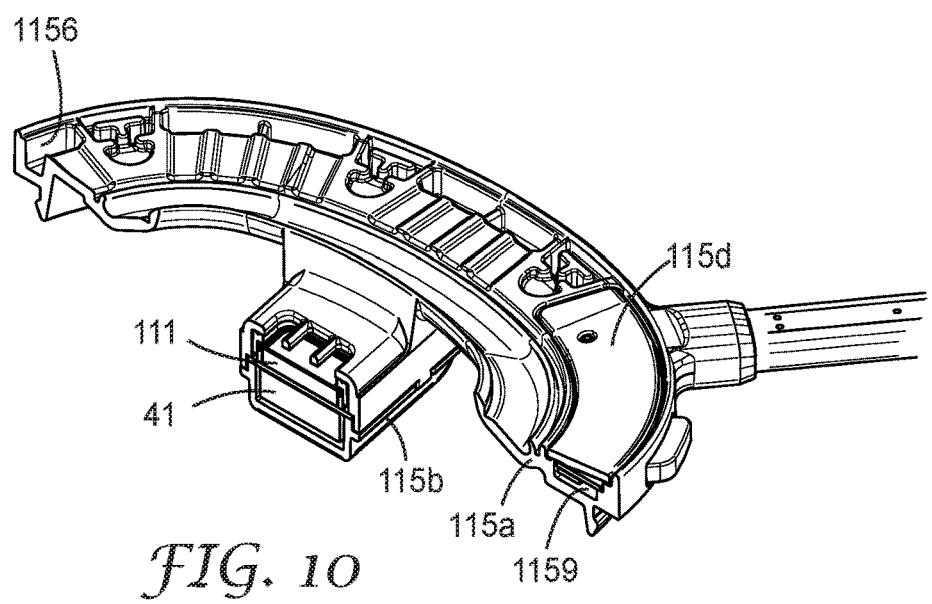
FIG. 10 is a cross-sectional view of the embodiment shown in FIG. 9.
Figure 11:
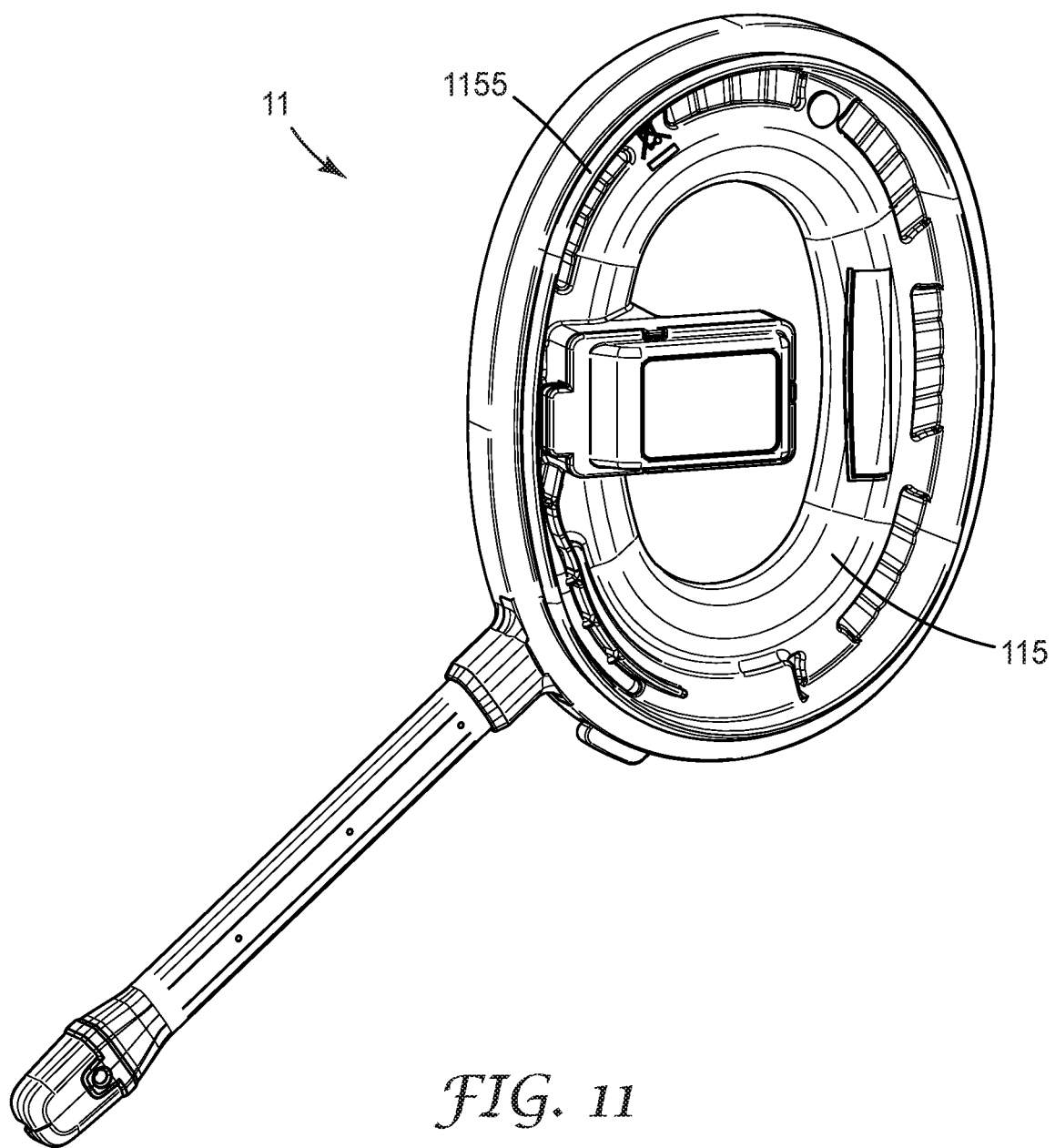
FIG. 11 is a rear view of the embodiment shown in 10.

FIG. 11 illustrates the active communication device 11 in a rear view. The support structure 115 of the active communication device 11 comprises a first retention structure 1155. The first retention structure 1155 in the example is formed by a circumferential flange. The support structure 115 further has a second retention structure 1156 (shown in FIG. 10) for retaining the cushioning. Alternatively or additionally the cushioning may be bonded to the support structure 115 by an adhesive. Accordingly, the active communication device 11 is configured for mounting between the cushioning and the outer shell of a hearing protector.

Figure 12:
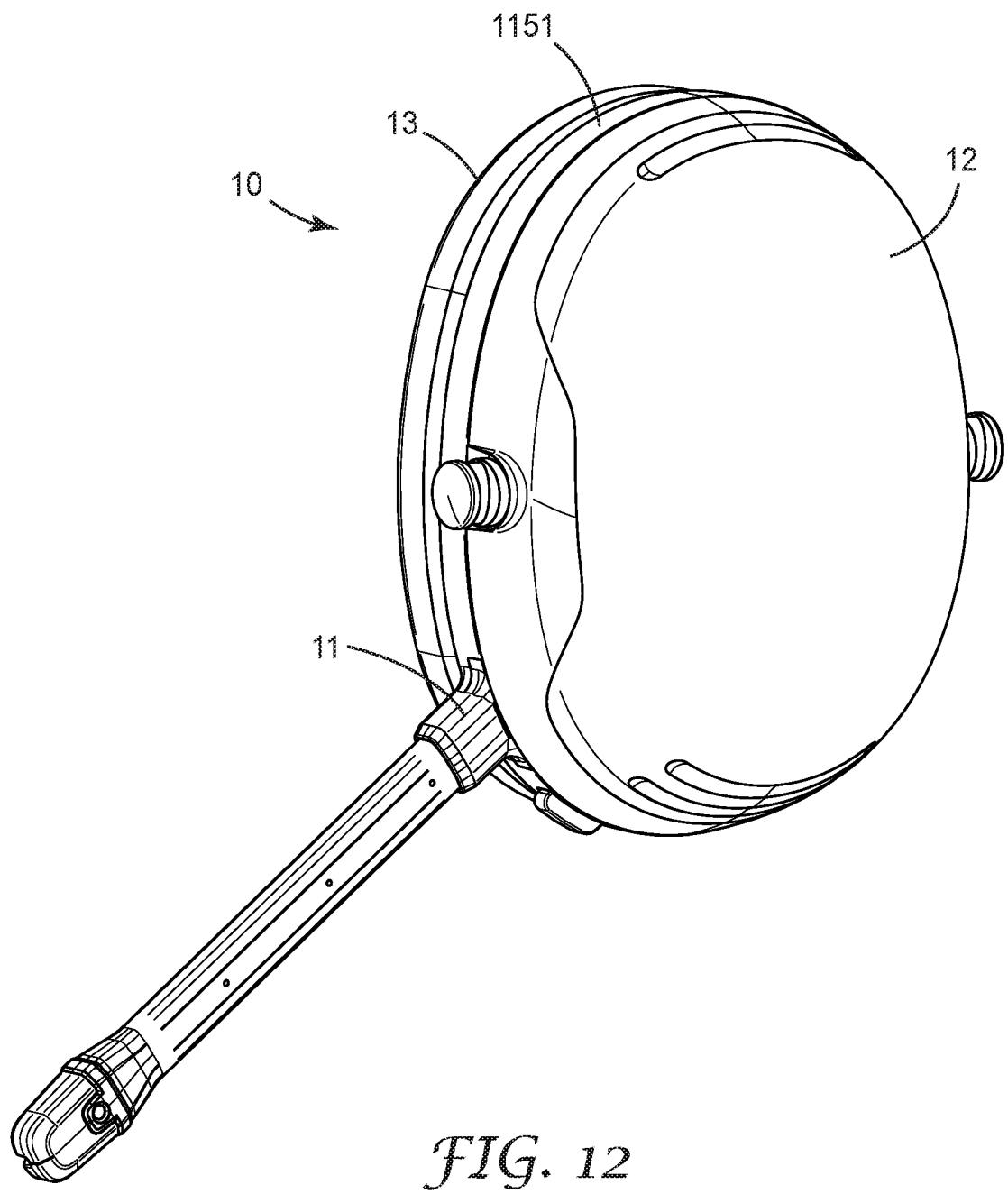
FIG. 12 is an assembly view of an earmuff according to an embodiment of the invention.

FIG. 12 shows the first earmuff 10 in which the active communication device 11 of FIGS. 9-11 is mounted between the outer shell 12 and the cushioning 13. Due to the fact that the electronic circuitry is entirely accommodated within boundaries of the mounting ring 1151 the earmuff 10 is relatively compact in design. Further, the electronic circuitry is protected against environmental impacts because the electronic circuitry is placed inside the boundaries of the earmuff 10.

The invention claimed is:

1. A method of retrofitting a hearing protector with an active communication device, the method comprising the steps of:
    providing a hearing protector that has two generally dome-shaped earmuffs, each earmuff forming toward an ear facing side of the earmuff a space for a wearer's ear, at least one of the earmuffs comprises an outer shell and a cushioning arranged adjacent the ear facing side;
    providing the active communication device, the active communication device comprising a loudspeaker and electronic circuitry which comprises a wireless communication interface, the electronic circuitry being configured to drive the loudspeaker based on information received via the wireless communication interface, wherein the active communication device comprises a mounting ring;
    mounting the mounting ring between the outer shell and the cushioning; and thereby
    retaining the active communication device at the hearing protector so that the loudspeaker is arranged within the space formed the earmuff.

2. The method of claim 1, wherein the earmuff comprises a spacer ring arranged between the cushioning and the outer shell, and wherein the method further comprises the step of replacing the spacer ring by the mounting ring.

3. The method of claim 1, wherein the active communication device further has a microphone, the microphone and the electronic circuitry being connected or connectable such that the electronic circuitry can receive information from the microphone and transmit the information via the wireless communication interface.

4. The method of claim 3, wherein the active communication device comprises a first part and a second part, the first part comprising the loudspeaker and the second part comprising the microphone, and wherein the second part is arranged outside the space formed by the respective earmuff.

5. The method of claim 4, wherein the first and second part form parts of one common structural entity.

6. The method of claim 3, wherein the first and second part are structurally separated and configured for a wireless communication with each other.

7. The method of claim 1, wherein the electronic circuitry is arranged inside boundaries of the mounting ring.

8. The method of claim 7, wherein at least a part of the electronic circuitry is arranged between the outer shell and the cushioning.

9. A hearing protector comprising:
    two generally dome-shaped earmuffs, each earmuff forming toward an ear facing side a space for a wearer's ear, wherein at least one of the earmuffs further comprises an outer shell and a cushioning arranged adjacent the ear facing side; and
    an active communication device comprising a loudspeaker and electronic circuitry which comprises a wireless communication interface, the electronic circuitry being configured to drive the loudspeaker based on information received via the wireless communication interface, and
    wherein the active communication device comprises a mounting ring that is retained between the outer shell and the cushioning, and wherein the loudspeaker is arranged within the space formed by one of the earmuffs.

10. The hearing protector of claim 9, wherein the mounting ring has a first retention structure being retained with a corresponding retention structure at the outer shell.

11. The hearing protector of claim 9, wherein the mounting ring and the cushioning are retained with each other.

12. The hearing protector of claim 9, wherein the active communication device comprises a microphone, the microphone and the electronic circuitry being connected or connectable such that the electronic circuitry can receive information from the microphone and transmit the information via the wireless communication interface.

13. The hearing protector of claim 9, further comprising a control button which is connected or connectable to the electronic circuitry for switching the microphone(s) on or off.

14. The hearing protector of claim 9, wherein the electronic circuitry is arranged inside boundaries of the mounting ring.

15. The hearing protector of claim 14, wherein at least a part of the electronic circuitry is arranged between the outer shell and the cushioning.

* * * * *